US006835216B2

United States Patent
Pratt et al.

(10) Patent No.: US 6,835,216 B2
(45) Date of Patent: Dec. 28, 2004

(54) CHAIN-BREAKING ANTIOXIDANTS

(75) Inventors: Derek A. Pratt, Nashville, TN (US); Luca Valgimigli, Forli (IT); Gino A. DiLabio, Aylmer (CA)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 09/891,671

(22) Filed: Jun. 26, 2001

(65) Prior Publication Data

US 2002/0143025 A1 Oct. 3, 2002

Related U.S. Application Data

(60) Provisional application No. 60/213,826, filed on Jun. 23, 2000.

(51) Int. Cl.[7] .................... C07D 239/47; C07D 239/52
(52) U.S. Cl. .................... 44/335; 252/401; 252/403; 252/404; 252/405; 544/298; 544/318; 544/330
(58) Field of Search ................. 514/272, 300, 514/302, 338, 335, 269; 544/298, 318, 330, 319; 546/113, 115, 122, 290; 44/335; 252/401, 403, 404, 405

(56) References Cited

U.S. PATENT DOCUMENTS

| | | | |
|---|---|---|---|
| 4,374,136 A | 2/1983 | Hill et al. ............... 424/251 |
| 4,554,276 A | 11/1985 | LaMattina ............... 514/272 |
| 4,711,888 A | 12/1987 | Walker et al. ............ 514/269 |
| 4,871,848 A | * 10/1989 | Treybig et al. ........... 544/224 |
| 5,001,136 A | 3/1991 | Walker ................... 514/336 |
| 5,010,193 A | 4/1991 | Maurer et al. ........... 544/243 |
| 5,177,079 A | 1/1993 | Connor et al. ........... 514/269 |
| 5,187,175 A | 2/1993 | Belliotti et al. .......... 514/269 |
| 5,196,431 A | 3/1993 | Belliotti et al. .......... 514/272 |
| 5,220,025 A | 6/1993 | Belliotti et al. .......... 544/298 |
| 5,284,949 A | 2/1994 | Belliotti et al. .......... 544/298 |
| 5,521,192 A | 5/1996 | Henrie, II et al. ......... 514/275 |
| 6,096,695 A | 8/2000 | Lam et al. ............... 508/570 |

OTHER PUBLICATIONS

Jovanovic, M. "Syntheses of some pyrimidine N–oxides", Can. J. Chem., Jun. 1984, vol. 62, No. 6, pp. 1176–1180.*
Pratt, et al., "Retarding the Oxidation of Electron–Rich Phenolic Compounds by Electron Transfer in Favour of Hydrogen–Atom Abstraction: Pyrimidinols as Antioidants?", Abstract for presentation at the Gomberg 2000 VIIIth Internataional Symposium on Organic Radical, Ann Arbor MI Jun. 25–29, 2000.
Pratt, et al., "5–Pyrimidinols: Novel Chain–Breaking Antioxidants More Effective Than Phenols", Journal of the American Chemical Society, 2000.

* cited by examiner

*Primary Examiner*—Richard L. Raymond
(74) *Attorney, Agent, or Firm*—Stites & Harbison PLLC; Richard S. Myers, Jr.

(57) ABSTRACT

Compounds, preferably 5-pyrimidinol and 3-pyridinol derivatives, that act as effective chain breaking antioxidants of both the lipid and water-soluble variety (analogous to the natural Vitamins E and C), many of which are more reactive toward peroxyl radicals than the most potent form of Vitamin E. These compounds may exhibit many chemopreventive effects associated with conditions in which free radical-mediated cellular damage or disruption is implicated and Vitamins E and C are shown to have protective effects. Additionally, these compounds should be excellent oxidation inhibitors as additives to fuels, lubricants, rubber, polymers, chemicals, solvents and foodstuffs.

29 Claims, 1 Drawing Sheet

CHAIN-BREAKING ANTIOXIDANTS

This application claims benefit of U.S. Patent Application Ser. No. 60/213,826 filed Jun. 23, 2000, entitled "Derivatives of 5-Pyrimidinols and 3-Pyridinols: Novel Chain-Breaking Antioxidants".

FIELD OF THE INVENTION

The present invention relates to compounds, including derivatives of 5-pyrimidinol and 3-pyridinol and any acid or base addition salt thereof, that are effective chain-breaking antioxidants both of the lipid and water-soluble variety and, in that regard, are analogous to the natural Vitamins E and C. Hence, not only will the compounds of the present invention be excellent oxidation inhibitors as additives to fuels, lubricants, rubber, polymers, chemicals, solvents and foodstuffs, but they may also exhibit many chemopreventive effects associated with cancer, aging, heart and lung disease, inflammation, Alzheimer's and Parkinson's disease, skin damage and any other conditions in which free radical-mediated cellular damage or disruption is implicated and in which Vitamins E and C and other antioxidants are shown to have protective effects.

BACKGROUND OF THE INVENTION

Autoxidation of hydrocarbons and other organic materials is one of the most important chemical processes known. Since the 1960's, the mechanism of inhibition of this process by antioxidants has been extensively studied, and antioxidants are now a key additive to many hydrocarbon products, including fuels, lubricant oils, rubber, polymers, chemicals, solvents and foodstuffs. However, it has only been in the last two decades that the importance of lipid peroxidation to human health has begun to become unearthed. Since then, substantial evidence has accumulated that implicate free radicals in aging, carcinogenesis and the pathogenesis of many conditions including heart disease (e.g. atherosclerosis), lung disease (e.g. emphysema) and several neurodegenerative disorders including Alzheimer's and Parkinson's diseases.

Consequently, the role of both enzyme and small-molecule antioxidants and the mechanisms of their protective function have been extensively studied. For example, it is now well accepted that the key initial event in the development of atherosclerosis involves free-radical mediated oxidative modification of low-density lipoprotein (LDL).

In support of this, it has been shown that a high intake of Vitamin E (-tocopherol, Formula 1 below), a potent lipid-soluble radical-trapping antioxidant, reduces the risk of coronary heart disease and that low levels of Vitamin E in serum correlate with an increased incidence of myocardial infarction. For example, see Gey, K. F. Nutr. Biochem., 1995, 6, 206–236, incorporated herein by reference.

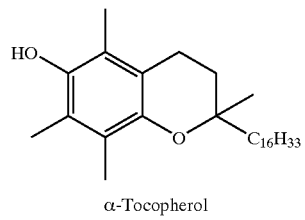

α-Tocopherol (Formula 1)

Furthermore, probucol (Formula 2, below), a radical-scavenging antioxidant, is widely used to treat hypercholesterolemia and atherosclerosis. For example, see Barkley et al. Drugs 1986, 37, 761–800.

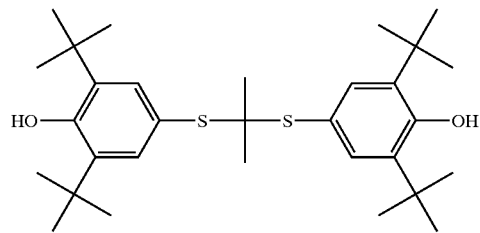

Probucol (Formula 2)

Given that antioxidants are of such tremendous industrial importance and have also been shown to possess preventive properties on the incidence of heart disease and many other degenerative diseases, various kinds of natural and synthetic antioxidants have been synthesized and studied both in vitro and in vivo. Unfortunately, few of them have demonstrated better radical-trapping activity than α-tocopherol, the major lipid-soluble radical-trapping antioxidant in plasma and LDL.

Phenols (of which α-tocopherol is an example) are the most abundant and widely used natural and synthetic antioxidants. Their mechanism of action as antioxidants, relies on their ability to transfer their phenolic H-atom to a chain-carrying peroxyl radical (LOO•, Reaction 1) at a rate much faster than that at which the chain-propagating step of lipid peroxidation proceeds (Reaction 2).

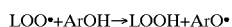
LOO•+ArOH→LOOH+ArO•    Reaction 1

LOO•+LH→LOOH+L•(+O$_2$→LOO•)    Reaction 2

A higher rate for Reaction 1 is expected with an increasingly weak ArO—H bond, and thus as the exothermicity of Reaction 1 increases relative to Reaction 2, one would expect that ArOH becomes a better chain-breaking antioxidant. Indeed, when the logarithm of the rate constant for Reaction 1 ($\log k_1$) is plotted against the phenolic O—H bond dissociation enthalpy (BDE) for several ArOH, a linear correlation of BDE (kcal/mol)=97.44–2.93 $\log k_1$(M$^{-1}$s$^{-1}$) is obtained. This correlation can be used to predict the rate constants for the reaction of peroxyl radicals with novel phenolic compounds whose O—H BDEs are known.

It is well-known that electron-donating (ED) groups substituted para and ortho to the phenolic hydroxyl lower the O—H bond dissociation enthalphy (BDE) and increase the rate of H-atom transfer to peroxyl radicals. However, efforts to design new phenolic antioxidants with increased rates of H-atom transfer to peroxyl radicals have remained unsuccessful. This is because, while the substitution of phenols with increasingly ED groups (e.g., —NH$_2$ and —NH$_2$) decreases their O—H BDEs, it also decreases their ionization potentials (IPs) such that they react directly with oxygen.

In 1985, Ingold and Burton investigated aminophenols as potential antioxidants. More specifically, they looked at Formula 3a and Formula 3b, below, as potential chain-breaking antioxidants, but found Formula 3a to be unstable in air and Formula 3b to react slowly with peroxyl radicals compared to -tocopherol. See Burton et al. J. Am. Chem. Soc. 1985, 107, 7053–7065, incorporated herein by reference.

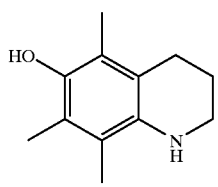

Formula 3a

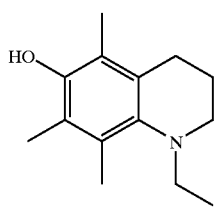

Formula 3b

These results may be explained in that the steric interaction between the meta-methyl and N-ethyl groups drives the N-ethyl group down out of the plane of the ring and removes the nitrogen lone pair from conjugation with the aromatic ring. This abolishes its stabilizing effect on the aryloxyl radical.

A known problem with aminophenols as antioxidants lies not only in the fact that they are very difficult to prepare and store, but also in their toxicity. In the case of para-aminophenol, this is related to its metabolic activation (oxidation, by cytochrome P450 among other possibilities) to a reactive intermediate that reacts with nucleophilic residues on proteins or DNA to form covalent intermediate that reacts with nucleophilic residues on proteins or DNA to form covalent intermediates or that can result in the depletion of glutathione stores.

Further substituted aminophenols (such as 4-N,N-dialkylaminophenol or 4b, above) are toxic because their oxidation no longer requires metabolism, but only a direct reaction with molecular oxygen to yield superoxide and the electrophilic species. This makes the compound a pro-oxidant and possible mutagen/carcinogen/teratogen rather than an antioxidant.

Based upon the above observations, the present inventors decided that a reasonable set of design criteria for new aminophenolic antioxidants are compounds with: (1) low phenolic O—H BDEs such that they have large log$k_1$ value, but (2) high ionization potentials (IPs) such that they are not reactive to molecular oxygen.

U.S. Pat. No. 4,554,276 to LaMattina discloses 2-amino-5-hydroxy-4-methyl pyrimidines that are disclosed as being useful as inhibitors of leukotriene synthesis and for the treatment of pulmonary, inflammatory and cardiovascular diseases, cancer and psoriasis, and peptide ulcers.

U.S. Pat. No. 4,711,888 to Walker discloses hydroxy or alkoxy pyrimidines that are disclosed as being inhibitors of leukotriene synthesis and, as a result, are useful in the treatment of pulmonary, inflammatory, allergic, cardiovascular diseases, and peptide ulcers.

U.S. Pat. No. 5,187,175 to Belliotti et al., discloses 2-carbonyl subtituted-5-hydroxy-1,3-pyrimidines that are disclosed as being useful as inhibitors of 5-lipoxygenase, and thereby providing a treatment for inflammation, arthritis, pain, fever, and the like.

U.S. Pat. No. 5,196,431 to Belliotti discloses 2-substituted amino-4,6-di-tertiarybutyl-5-hydroxy-1,3-pyrimidines described as having activity as inhibitors of 5-lipoxygenase and/or cyclooxygenase providing treatment for inflammation, arthritis, pain, and fever.

U.S. Pat. No. 5,220,025 to Belliotti et al. is a divisional of the '431 patent discussed above.

U.S. Pat. No. 5,001,136 to Walker discloses 2-substituted methylamino-amino 5-(hydroxy or alkoxy) pyridines useful in the treatment of pulmonary, inflammatory, dermatological, allergic and cardiovascular diseases.

U.S. Pat. No. 5,284,949 to Belliotti et al. discloses 2-substituted amino-4,6-di-tertiarybutyl-5-hydroxy-1,3-pyrimidines described as having activity as inhibitors of 5-lipoxygenase and/or cyclooxygenase providing treatment for inflammation, arthritis, pain, and fever.

U.S. Pat. No. 5,177,079, to Connor et al. describe 2-substituted-4,6-di-tertiary-butyl-5-hydroxyl-1,3-pyrimidines disclosed as being useful as inhibitors of 5-lipoxygenase and/or cyclooxygenase providing treatment of conditions advantageously affected by such inhibition including inflammation, arthritis, pain, fever.

SUMMARY OF THE INVENTION

The present invention relates to compounds, including derivatives of 5-pyrimidinol and 3-pyridinol and any acid or base addition salt thereof, that are effective chain-breaking antioxidants both of the lipid and water-soluble variety, and in that regard, are analogous to natural Vitamin E and C.

The present inventors have discovered that many 5-pyrimidinol and 3-pyridinol derivatives act as effective chain-breaking antioxidants in vitro. Their synthesis precludes that they may be prepared easily as either of the lipid- or water-soluble variety (analogous to the natural Vitamins E and C). Furthermore, compounds of the present invention may be significantly more reactive toward peroxyl radicals than the most potent form of Vitamin E (α-tocopherol). Furthermore, the compounds of the present invention are stable to air oxidation. In addition to their industrial applications, compounds of the present invention exhibit many chemopreventive effects associated with cancer, aging, heart and lung disease, inflammation, Alzheimer's and Parkinson's disease and any other conditions in which free radicals are implicated as being involved in their pathogenesis.

Additionally, the compounds of the present invention are excellent oxidation inhibitors as additives to fuels, lubricants, rubber, polymers, chemicals, solvents and foodstuffs.

Accordingly, an object of the present invention is to provide a compound of the following formula, and acid or base addition salts thereof:

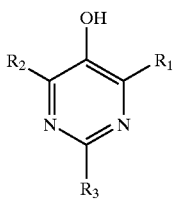

Formula 4 wherein, $R_1$ is selected from the group consisting of hydrogen, alkyl, amino, alkylamino, N,N-dialkylamino;

$R_2$ is selected from the group consisting of hydrogen, alkyl; and $R_3$ is an electron-donating substituent.

Another object of the present invention is to provide a compound of the following formula, and acid or base addition salts thereof:

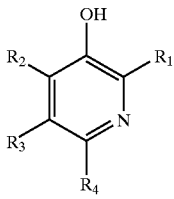

Formula 5 wherein, $R_1$ is selected from the group consisting of hydrogen, and, alkyl;

$R_2$ is selected from the group consisting of hydrogen, and alkyl;

$R_3$ is selected from the group consisting of hydrogen, and alkyl; and $R_4$ is an electron-donating substituent.

Another object of the present invention is to provide a compound of the following formula, and acid or base addition salts thereof:

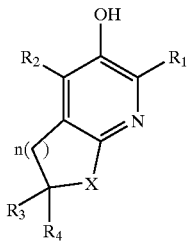

Formula 6 wherein,

X is N—$R_5$ or O;

$R_1$ is selected from the group consisting of hydrogen, and, alkyl;

$R_2$ is selected from the group consisting of hydrogen, alkyl;

$R_3$ is selected from the group consisting of hydrogen, alkyl;

$R_4$ is selected from the group consisting of hydrogen, alkyl;

$R_5$ is selected from the group consisting of hydrogen, alkyl; and n is 1 or 2.

Another object of the present invention is to provide a method of inhibiting the oxidation of compounds or mixtures comprising the addition of an effective amount of at least one of the above compounds to the compound or mixture.

Another object of the present invention is to provide a method of reducing the oxidative environment in a petroleum composition selected from the group consisting of lubricating compositions and liquid organic fuels, said method comprising adding to said petroleum composition an effective amount of an antioxidant composition, said antioxidant composition comprising at least one of the above compounds.

Another object of the present invention is to provide a method of inducing antioxidant activity in warm-blooded animals comprising administering to warm-blooded animals an antioxidatingly effective amount of a biologically active composition, the biologically active composition comprising at least one of the above compounds.

Finally, another object of the present invention is to provide a method of treating free radical-mediated cellular damage in warm-blooded animals, comprising administering to warm-blooded animals an antioxidatively effective amount of at least one of the above compounds.

DESCRIPTION OF THE PREFERRED EMBODIMENTS

Figure 1:
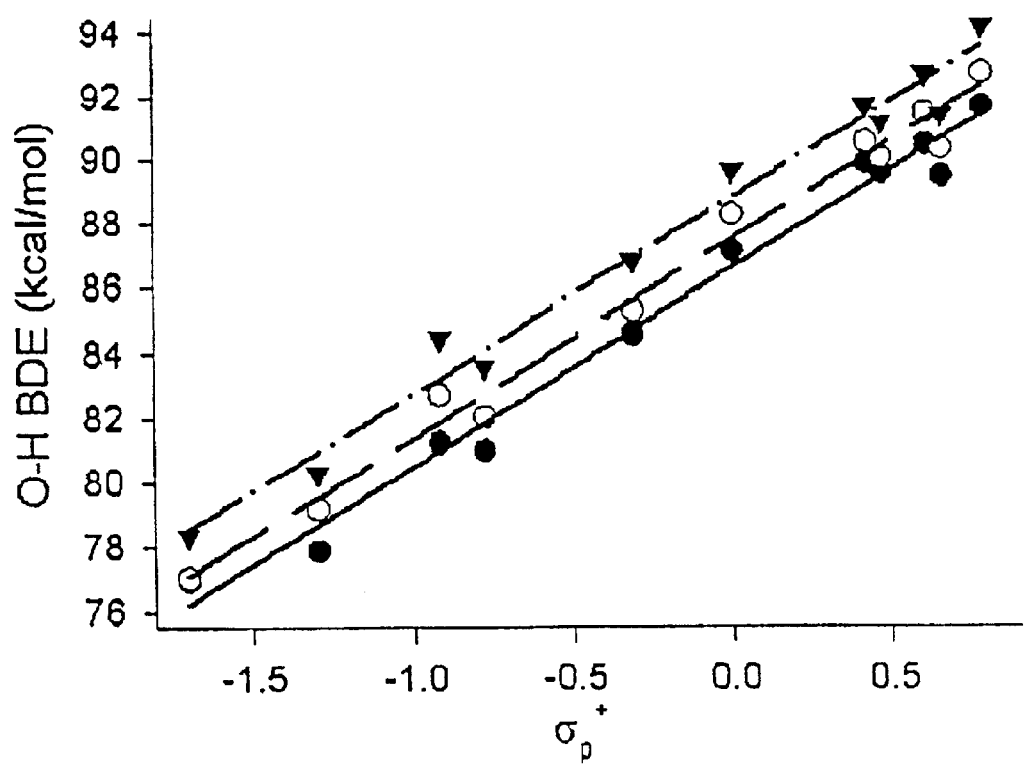
FIG. 1 shows correlations of $\sigma_p^+$ and the calculated gas phase O—H bond dissociation enthalpies (298K) of 4-substituted phenols (•), 6-substituted-3-pyridinols (○), and 2-substituted-5-pyrimidinols (▼).

As stated above, an object of the present invention is to provide compounds that are chain-breaking antioxidants. Without being bound by theory, incorporating nitrogen into the aromatic rings of phenolic compounds, has the effort of stabilizing the parent phenol (by lowering the highest occupied molecular orbital energy) while destabilizing the radical cation, thereby effectively raising the IP. The effect of nitrogen in the aromatic ring would not greatly affect the O—H BDE because the effects on the parent and radical should be similar. Furthermore, a pyrimidine or pyridine ring may better stabilize a partial negative charge on the phenolic oxygen, which would result in a favorable polar effect in the transition states of hydrogen atom transfer reactions. The greater charge separation would bring about a faster rate of reaction of alkyl, alkoxyl and peroxyl radicals with these compounds over phenols with the same O—H BDE.

Using density functional theory model calculations recently developed by DiLabio and co-workers (see: DiLabio et al., J. Phys. Chem. A. 1999, 103, 1653–1661 and DiLabio et al. J. Org. Chem. 2000, 65, 2195–2203) and experimental measurements recently developed by Pedulli and co-workers (largely summarized in Lucarini et al., J. Am. Chem. Soc. 1999, 121, 11546–11553) the reactivity of model 5-hydroxypyrimidine (5-pyrimidinol) and 3-hydroxypyridine (3-pyridinol) derivatives can be studied. For example, the present inventors have found that many of the compounds of the present invention have lower O—H BDEs than Vitamin E, but higher or similar IPs. This suggests that many of the compounds of the present invention should be at least as stable to air oxidation but yet more reactive to peroxyl and alkyl radicals than similarly substituted phenols.

Furthermore, the reactivities of the compounds of the present invention with alkyl and peroxyl radicals indicate the presence of an anticipated polar effect in the transition state. Making the compounds of the present invention with the same O—H BDE's as phenolic compounds better chain-breaking radical-trapping antioxidants.

Compounds of the present invention include compounds of formulae 4–6, below:

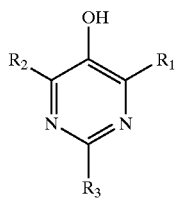

Formula 4

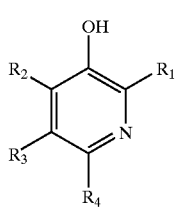

Formula 5

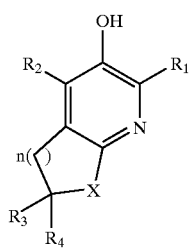

Formula 6

Preferred derivatives of Formula 4 can be divided into 2 groups. They include, but are not limited to those in group a: 2-$R_3$-4-$R_2$-6-$R_1$-5-hydroxypyrimidines where $R_1$, $R_2$=H or alkyl; $R_3$=any electron-donating group, but most preferably alkoxy, amino, N-alkylamino or N,N-dialkylamino; and those of group b: 2-$R_3$-4-$R_2$-6-$R_1$-5-hydroxypyrimidines where $R_1$=amino, N-alkylamino, or N,N-dialkylamino; $R_2$=H or alkyl; $R_3$=any electron donating group, but most preferably alkoxy, amino, N-alkylamino or N,N-dialkylamino. These preferred derivatives are calculated to be at least 10 kcal/mol more stable than their 1,4-tautomers or 1,2-tautomers.

Preferred derivatives of Formula 5 include but are not limited to 2-$R_1$-4-$R_2$-5-$R_3$-6-$R_4$-3-hydroxypyridines where $R_1$, $R_2$, $R_3$=H or alkyl and $R_4$=any electron donating group, but most preferably alkoxy, amino, N-alkylamino or N,N-dialkylamino.

With regard to preferred alkyl groups adjacent to the active hydroxyl group in Formula 4 and Formula 5, and not being bound by theory, it is believed that the tertiary-butyl groups result in a lower O—H BDE, but hinder the approach of peroxyl radicals or other substrates to the pyrimidinoxyl radical—this is important in preventing tocopherol-mediated peroxidation. The preferred methyl groups result in a slightly higher O—H BDE, but there is no steric hindrance to the approach of peroxyl radicals or other substrates to the aryloxyl radicals. The preferred alkyl groups on the exocyclic amine group are varied from hydrogen to methyl to ethyl for greater electron-donation and hence weakening of the O—H bond. The tertiary-butyl group has the potential to hinder any possible N-oxidation to the N-oxide by cytochrome P450 or N-methylation by N-methyl transferases although little precedent for this exists in the literature. Pentyl, octyl and phytyl groups make the compound increasingly lipid-soluble. Di-pentyl and di-octyl compounds allow for greater mobility within and between membranes compared to Vitamin E. The di-phytyl moiety firmly incorporates and retains the molecule in the membrane or lipoprotein particle.

Preferred derivatives of Formula 6 are for n=2, X=N—$R_5$ (6-hydroxy-2-$R_3$-2-$R_4$-5-$R_2$-7-$R_1$-1-$R_5$-2,3,4-trihydro-[1,8]-naphthiridine) and n=1, X=N—$R_5$ (5b-hydroxy-2-$R_3$-2-$R_4$-4b-$R_2$-6b-$R_1$-1-$R_5$-pyrrolo-[2,3-b]-pyridine) are quinoline and indole derivatives of pyridines where $R_1$, $R_2$, $R_3$, $R_4$, $R_5$=H or alkyl. Derivatives where n=2 or 1 and X=O and $R_1$, $R_2$, $R_3$, $R_4$=H or alkyl may also be particularly useful.

Preferably, with respect to Formulas 4–6, above, preferred substituents are electron-donating groups that may donate via direct conjugation or hyperconjugation, electron density to the aromatic ring, thereby destabilizing the molecular orbitals of π-symmetry in the parent, and stabilizing them in the radical. For example, any substituent group whose Hammett substituent constant, sigme-plus, is less than zero. See Hansch et al., Chem. Rev., 1991, 91, 165–195. Electron-donating substituent groups include but are not limited to alkyl, phenyl, alkoxy, acyloxy, hydroxy, amino, alkylamino, dialkylamino.

Preferred compounds of Formula 4, above, include compounds of Formulae 7 and 9, below. Preferred compounds of Formula 5, above, include compounds of Formula 8 below.

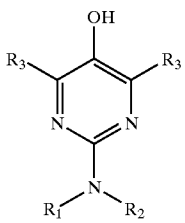

Formula 7

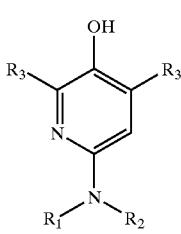

Formula 8

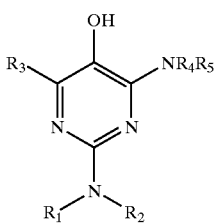

Formula 9

Preferred derivatives of formula 7 and 8 are 2-N,N—$R_1$,$R_2$-amino-4-$R_3$-6-$R_3$-5-hydroxypyrimidines ($R_1$, $R_2$=H, methyl, ethyl, t-butyl, pentyl, octyl, phytyl; $R_3$=H, methyl, t-butyl) and 4-N,N—$R_1$,$R_2$-amino-2-$R_3$-3-hydroxypyridines ($R_1$=H, methyl, ethyl, t-butyl, pentyl, octyl, phytyl; $R_2$=H, methyl, ethyl, t-butyl, pentyl, octyl, phytyl; $R_3$=H, methyl, t-butyl), respectively.

With regard to the preferred alkyl groups ortho to the hydroxyl group, and not being bound by theory, it is believed that the t-butyl groups result in a lower O—H BDE, but hinder the approach of peroxyl radicals or other substrates to the pyrimidinoxyl radical—this is important in preventing tocopherol-mediated peroxidation. The preferred methyl groups result in a slightly higher O—H BDE, but there is no steric hindrance to the approach of peroxyl radicals or other substrates to the pyrimidinoxyl radicals. The preferred alkyl groups on the exocyclic amine group are varied from hydrogen to methyl to ethyl for greater electron-donation and hence weakening of the O—H bond. The preferred t-butyl group has the potential to eliminate any possible N-oxidation to the N-oxide by cytochrome P450 or N-methylation by N-methyl transferases although little precedent for this exists in the literature. The preferred pentyl, octyl and phytyl groups make the compound increasingly lipid-soluble. The di-pentyl and di-octyl compounds allow for greater mobility within and between membranes compared to Vitamin E. The di-phytyl moiety firmly incorporates and retains the molecule in the membrane or lipoprotein particle.

Preferred derivatives of Formula 9 (2-N,N—$R_1,R_2$-amino-6-$R_3$-4-N,N—$R_4,R_5$-amino-5-hydroxypyrimidine) are $R_1$=H, methyl, ethyl, t-butyl, pentyl, octyl, phytyl; $R_2$=H, methyl, ethyl, t-butyl, pentyl, octyl, phytyl; $R_3$, $R_4$, $R_5$=H, methyl, t-butyl). It is believed that these preferred derivatives compounds are 10 kcal/mol more stable than their 1,4-tautomers, and that the 3-hydroxypyridines (6, 8, 9) are 8–10 kcal/mol more stable than their amide tautomers.

Preferred embodiments of Formula 6, above, include compounds of Formulae 10 and 11, below.

Formula 10

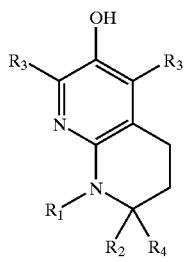

Formula 11

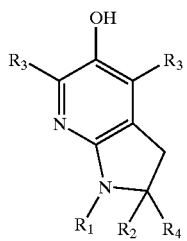

Preferred derivatives of compounds 10 (6-hydroxy-2-$R_2$-2-$R_4$-5-$R_3$-7-$R_3$-1-$R_1$-2,3,4-trihydro-[1,8]-naphthiridine) and 11 (5b-hydroxy-2-$R_2$-2-$R_4$-4b-$R_3$-6b-$R_3$-1-$R_1$-pyrrolo-[2,3-b]-pyridine) are quinoline and indole derivatives of pyridines ($R_1$=H, methyl; $R_2$=H, methyl, ethyl, t-butyl, pentyl, octyl, phytyl; $R_4$=H, methyl, ethyl, t-butyl, pentyl, octyl, phytyl; $R_3$=H, methyl, t-butyl, hydroxy). $R_3$ may also be hydrogen because it may be important for at least one position to be kept vacant so that hemolytic aromatic substitution, for example by nitrogen dioxide, can occur, and the adduct could be subsequently eliminated.

The synthesis of 5-pyrimidinols has been described both in the scientific and patent literature. Simple compounds such as 5-pyrimidinol itself can be obtained readily via displacement of the appropriately substituted 5-bromopyridine with methoxide in methanol, followed by deprotection to yield the 5-pyrimidinol (see EXAMPLE 1, below, and Bredreck et al. Chem. Ber. 1958, 91, 2832). Alternatively, the bromide can be converted to the hydroxyl directly upon treatment with barium hydroxide and a copper catalyst (see Bray et al. Biochem. J. 1951, 48, 400). A variety of 2,4,6-alkyl-substituted-5-pyrimidinols can be prepared from substituted 5-carbonyloxazoles (see EXAMPLES 2 and 3, below, and Dornow and Hell Chem Ber. 1960, 1998) or from the appropriately substituted 5-bromopyrimidines as described above. Additionally, a variety of 4-alkoxy-substituted-5-pyrimidinols can be prepared from condensation of 3-acyloxy-2,4-pentanediketones with O-alkylisoureas, as shown in EXAMPLE 4, below.

Furthermore, from appropriately-substituted pentanediketones, a variety of amino and dialkyl amino substituted-5-pyrimidinols can be obtained upon condensation with 1,1-dialkylguanidines similar to in EXAMPLE 4 (see EXAMPLE 5) or again, the bromide can be converted to the hydroxyl as described above. Ortho-amine substituted-5-pyrimidinols (9) can be prepared from the appropriately substituted precursor with a vacant ortho position and subjected to Chichibabin conditions, i.e., amination by alkali-metal amides (for a review, see: Vorbruggen Adv. Heterocycl. Chem. 1990, 49, 117–192).

The synthesis of 3-pyridinols have also been well documented in the literature. Simple 3-pyridinols can either be purchased from commercial sources or prepared from the precursor 3-bromopyridine analogous to the synthesis of 5-pyrimidinols from 5-bromopyrimidines. The more complex substitution patterns may be achieved by someone skilled in the art, in a variety of ways described in the scientific literature (see, for example: Pyridine and its Derivatives, Part 3, Erwin Klingsberg, Ed. Interscience Publishers, 1962). For example, 6-amino-2,4-dimethyl-3-hydroxypyridine may be prepared from the Diels Alder reaction of methacrylonitrile and 2-amino-5-methyloxazole (see: Hayakawa et al. Chem. Pharm. Bull. 1984, 32, 4914). Alternatively, treatment of the 6-amino-2,4-dimethyl-3-bromopyridine with barium hydroxide in the presence of a copper catalyst yields the product [see: Bray et al., Biochem. J. 1951, 400). Compounds such as 6, 10 and 11 can be prepared from the lithiation of the 2-amino pyridine, followed by treatment with a terminal dibromoalkane.

The following examples are given for illustrative purposes and are not intended to be limiting the present invention.

EXAMPLE 1

5-Pyrimidinol

Preparation of 5-methoxypyrimidine

A Parr bomb is charged with 15 g (0.094 mol) of 5-bromopyrimidine and 5.4 g (0.10 mol) of sodium methoxide in 170 ml of methanol. The whole is heated at 100–120° C. for 16 hours. The deep brown mixture is neutralized with glacial acetic acid and extracted three times with ether. The combined organic layers are then dried over $Na_2SO_4$ and concentrated in vacuo. The resulting brown solid is purified by column chromatography on silica gel using 9:1 ethyl acetate:hexane as eluent. The pyrimidine is thus obtained as pale yellow crystals (7 g, 70%). Alternatively, purification can be accomplished by distillation bp(10 mm/Hg) 76°.

Preparation of 5-pyrimidinol

In a three-necked flask cooled with ice is poured 3.38 g sodium hydride (3.38 g, 140.9 mmol) as a 60% suspension in mineral oil and dry DMF (60 ml). Ethanethiol (4.38 g, 70.48 mmol) is added dropwise and evolution of hydrogen is observed. After 15 minutes, 5-methoxypyrimidine (3.8 g, 35.3 mmol) is added and the resulting mixture is heated at 100° C. for 4 hours. A generous stream of argon is bubbled through during the reaction, and the head of the reflux condenser is connected with a cold trap charged with mCPBA in dichloromethane (in order to trap and oxidize the sulfide produced). The deep brown suspension is cooled with ice and the reaction is quenched with water (100 ml) neutralized with acetic acid and partitioned with ethyl acetate (4×100 ml). The organic layers are dried in vacuo and the residual yellow solid is purified by column chromatography using ethyl acetate as eluent. The compound is thus obtained as white needles. A yellow color is due to the presence of methyl-ethylsulfide and could be crystallized from dioxane to yield 1.7 g in 50% yield.

EXAMPLE 2

2,4,6-Trimethyl-5-pyrimidinol

Preparation of 2,4-dimethyl-5-acetyloxazole

Chloroacetylacetone 8 g (59.4 mmol) is dissolved in 70 ml of glacial acetic acid and ammonium acetate 13.7 g (178.2 mmol) is then added and the mixture is refluxed for 4 hours. The solution is cooled, brought to pH 5 and extracted into ether; the organic layer is dried over $Na_2SO_4$ and concentrated to dryness in vacuo. The residue is purified by column chromatography on silica gel using 8:2 hexane-:ethyl acetate as eluent. The 2,4-dimethyl-5-acetyloxazole is obtained as orange needles (2.2 g, 27%).

Preparation of 2,4,6-trimethyl-5-pyrimidinol

The 2,4-dimethyl-5-acetyloxazole is poured into a Parr Bomb with 20 ml (51 mmol) of concentrated ammonium hydroxide and brought to 180° C. in three hours. Heating is continued for 10 hours, and after cooling the mixture is brought to pH 5 with HCl, extracted into ether, dried over $Na_2SO_4$ and stripped in vacuo. The residual solid is crystallized from benzene to give pale yellow crystals (1.3 g, 60%).

EXAMPLE 3

2-Methyl-4,6-di-tert-butyl-5-pyrimidinol

Preparation of 2-methyl-4-tert-butyl-5-tert-butyl carbonyl oxazole

4-Bromo-2,2,6,6-tetramethylheptane-3,5-dione (1.5 g, 5.7 mmol) prepared according to the method reported by Shoppe and Stevensons, J. Chem. Soc. Perk. Trans. I 3015 (1972) is dissolved in glacial acetic acid (60 ml); ammonium acetate (2.6 g 34.2 mmol) is added and the mixture is refluxed 27 hours. The clear orange solution is diluted with water (60 ml), brought to pH 5 with NaOH 0.5 M and extracted with ethyl acetate (3×25 ml). The organic phase is dried with sodium sulfate and evaporated in vacuo. The oxazole is thus obtained as a deep orange oil, later purified on a pad of silica gel eluted with hexane/ethyl acetate 8:2. The yield was 1.25 g (98%).

Preparation of 2-methyl-4,6-di-tert-butyl-5-pyrimidinol

The 2-methyl-4-tert-butyl-5-tert-butyl carbonyl oxazole (1.25 g, 5.6 mmol) is poured into a Parr Bomb with concentrated ammonium hydroxide (100 ml) and heated at 180° C. for 36 hours. The excess ammonia is evaporated and the pH of the solution is adjusted to 6 with 37% HCl; the resulting solution is extracted into ether (3×25 ml) and the organic layer is dried with sodium sulfate and evaporated in vacuo. Chromatography on silica gel eluting with 8:2 hexane:ethyl acetate afforded the desired pyrimidine as white crystals (0.87 g, 70%).

EXAMPLE 4

2-Methoxy-4,6-dimethyl-5-pyrimidinol

Preparation of benzoic acid 1-acetyl-2-oxo-propyl ester

Sodium benzoate (106.5 g, 0.74 mol) is suspended in 500 ml of dry DMSO in a three necked flask equipped with a mechanical stirrer and under a gentle stream of argon. Chloroacetylacetone (50 g, 0.37 mol) is then added and the resulting orange mixture is stirred vigorously. After 3 hours the reaction is complete (TLC hexane/ethyl acetate 8/2); the melange is cooled by means of iced water and diluted with 500 ml of water. The solution is then extracted into ether (3×400 ml), washed with water (2×1 L), dried over $Na_2SO_4$ and concentrated to dryness in vacuo. The resulting viscous orange oil is pure enough for the next step. The yield is 81.4 g (100%).

Preparation of 2-methoxy-4,6-dimethyl-5-benzyloxy pyrimidine

The benzoic acid 1-acetyl-2-oxo-propyl ester 3.2 g (14.9 mmol) is dissolved in 50 ml of dry DMF in a three-necked flask under argon. Sodium acetate 2.4 g (29.8 mmol) and O-methyl isoureahydrogensulfate 2.56 g (14.9 mmol) are then added and the mixture is heated at 65° C. for 24 hours. The reaction mixture is cooled with ice and quenched with water, and then neutralized with glacial acetic acid and extracted into ether. The organic layer is dried over $Na_2SO_4$ and concentrated to dryness in vacuo. The residual solid is purified by column chromatography on silica gel using 8:2 hexane:ethyl acetate as eluent. The yield is 0.7 g (20%).

Preparation of 2-methoxy-4,6-dimethyl-5-pyrimidinol

The 2-methoxy-4,6-dimethyl-5-benzyloxy pyrimidine 0.7 g (2.7 mmol) is dissolved in 10 ml of ethanol with 0.3 g (5.4 mmol) of KOH. The whole is refluxed for 11 hours, and after cooling the reaction is diluted with 20 ml of water and brought to pH 5 with glacial acetic acid. The mixture is extracted into ethyl acetate (3×25 ml), dried over $Na_2SO_4$ and stripped in vacuo. The resulting solid is purified by column chromatography on silica gel using 9:1 hexane:ethyl acetate as eluent. The yield is 0.4 g (98%).

EXAMPLE 5

2-N,N-Dimethylamino-4,6-dimethyl-5-pyrimidinol

Preparation of 3-acetoxy-2,4-pentan-2,4dione 3-chloro-2,4pentanedione (10 g 74.6 mmol) is dissolved in dry DMSO; sodium acetate (12.2 g 149.2 mmol) is added and the mixture is kept at room temperature. After a few minutes the solution turns a deep orange-red color, and after two hours is complete. Water is added, the solution is partitioned with ether (3×50 ml) and the combined organic layers are dried with sodium sulfate and evaporated in vacuo. The resulting orange oil is purified on a pad of silica gel eluting with 8:2 hexane:ethyl acetate. The yield is 9.2 g (80%).

Preparation of N,N-dimethylamino-4,6-dimethyl-5-pyrimidinol

The titled acetoxyketone (1 g, 6.3 mmol) is dissolved in dry DMF under a nitrogen atmosphere; sodium acetate (1 g 12.6 mmol) and 1,1-dimethylguanidine sulfate (1.7 g, 6.3 mmol) are added and the mixture is kept at 100° C. for 4 h.

The resulting orange suspension is diluted with water and extracted with ethyl acetate (3×25 ml), the organic layer is dried with sodium sulfate and evaporated in vacuo. Purification by chromatography (8:2 hexane:ethyl acetate) gave a yellow oil which crystallized on cooling; yield 50%. Deacetoxylation with alcohlic NaOH afforded the pyrimidinol in 50% of yield (yellow needles from benzene/light petroleum benzene).

TABLE A

Properties of Examples Important for Antioxidant Efficacy.
O—H BDE: O—H bond dissociation enthalpy; k/alkyl: second order rate constant for reaction with alkyl radicals; k/peroxyl: second order rate constant for reaction with peroxyl radicals.

| Example | O—H BDE | k/alkyl | k/peroxyl |
|---|---|---|---|
| 1 | 91.3[a] | $3.6 \times 10^6$ | b |
| 2 | 85.2 | $4.6 \times 10^5$ | $3.3 \pm 0.4 \times 10^4$ |
| 3 | 84.1 | $3.2 \pm 0.5 \times 10^4$ | $2.2 \pm 0.3 \times 10^4$ |
| 4 | 82.5 | c | c |
| 5 | 78.2 | $2.9 \pm 1.1 \times 10^6$ | $8.6 \pm 0.5 \times 10^6$ |

[a]Estimate based upon other results to date for other 5-pyrimidinols.
[b]No induction period.
[c]Not performed.

As stated above, it is well-known that electron-donating (ED) groups substituted para and ortho to the phenolic hydroxyl lower the O—H bond dissociation enthalphy (BDE) and increase the rate of H-atom transfer to peroxyl radicals. However, efforts to design new phenolic antioxidants with increased rates of H-atom transfer to peroxyl radicals have remained unsuccessful. See, for example, Burton et al., *J. Am. Chem. Soc.*, 1985, 107, 7053–7065; and Wright et al., *Cancer Detect. Prev.*, 1988, 22, 204.

For example, an aza-analogue of α-TOH (compound (ii), below) and 9-hydroxy-julodine (compound (iii), below) were both unsatisfactory when used as antioxidants because they reacted directly with oxygen via electron transfer. In an effort to increase the stability of highly reactive, electron-rich phenols under conditions where oxygen is present, the present inventors incorporated nitrogen into the phenolic ring.

Compounds

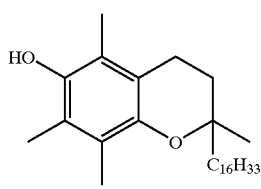

(i)

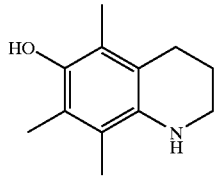

(ii)

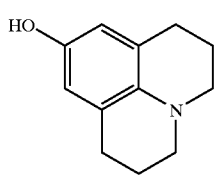

(iii)

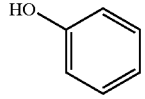

(iv)

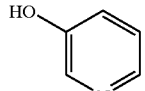

(v)

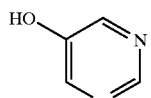

(vi)

The present inventors have developed a density functional theory (DFT) model ((RO)B3LYP/6-311+G(2d,2p)//AM1/AM1) which predicts X—H bond energetics (X=C,N,O, and S) for several types of compounds, including phenols, generally to within experimental error. See DiLabio et al., *J. Phys. Chem. A.*, 1999, 103, 1653–1661. A second model, (B3LYP/6-31G(d)//AM1/AM1), evaluates the IPs of polysubstituted aromatics. See DiLabio et al., *J. Org. Chem.*, 2000, 65, 2195–2203. Using these two DFT models, the substituent effects on the O—H BDEs and IPs of 3-pyridinol (v) and 5-pyrimidinol (vi) can be calculated relative to those we have for phenol (iv).

While substitution of N for C at the 3-position of (iv) to give (v) increases the calculated IP from 195.4 to 206.4 kcal/mol (87.1 to 88.2 kcal/mol). Introducing a second N at the 5-position to give (iv) further raises the IP and O—H BDE to 219.7 and 89.6 kcal/mol, respectively. Thus, despite the increase in IP of 24.3 kcal/mol from (iv) to (vi), the O—H BDE increases by only 2.5 kcal/mol. When the effects of para-substituents on the IPs and O—H BDEs in phenols, 6-substituted-3-pyridinols, and 2-substituted-5-pyrimidinols are calculated, it is found that the substituent effects on their O—H BDEs (FIG. 1) and IPs (not shown) are conserved.

Finally, the O—H BDEs and IPs of further-substituted 5-pyrimidinols were calculated (the 3-pyridinols will be considered separately in a forthcoming publication). The results are presented in Table 1, below, along with those of their phenolic analogues and α-TOH for comparison.

TABLE 1

Calculated Substituent Effects on Gas Phase O—H BDEs at 298 K and Adiabatic IPs at 0 K of Symmetrically Substitued Phenols (4) and 5-Pyrimidinols (6)[a]

| 2 × ortho | para | 6 | 4 |
|---|---|---|---|
| H | H | (89.6)/(219.7) | (87.1)/(195.4) |
| H | CH$_3$ | −2.8/−10/4 | −2.5/−8.5 |
| CH$_3$ | CH$_3$ | −6.4/−22.7 | −6.7/−17.1 |
| H | OCH$_3$ | −6.0/−21.6 | −6.1/−18.9 |
| CH$_3$ | OCH$_3$ | −9.8/−31.4 | −10.1/−26.2 |
| H | N(CH$_3$)$_2$ | 11.3/−45.1 | −10.1/−37.7 |
| CH$_3$ | N(CH$_3$)$_2$ | −15.5/−52.7 | −14.8/−43.1 |
| a-TOH (1) | | | |

[a]Data presented BDE/IP in kcal/mol. Absolute values for unsubstituted 6 and 4 are in parentheses.

Increasing both the number and strength of ED substituents in the ortho and para positions brings about a steady decrease in the O—H BDE and IP. Consistent with the data in FIG. 1, the substituent effects on both the O—H BDE and IP are roughly the same for both compounds.

Our calculations suggest that 5-pyrimidinols should be effective H-atom donors with the advantage of being much more stable to air oxidation than similarly substituted phenols. To confirm this, we prepared four 5-pyrimidinols (vi(a)–vi(d)) as per procedures set forth by Bredereck et al., *Chem. Ber.,* 1958, 91, 2832; Dornow et al., *Chem. Ber.,* 1960, 93, 1998; Conner et al., U.S. Pat. No. 5,117,079; and Walker et al., U.S. Pat. No. 4,711,888; respectively. The O—H BDEs were measured by EPR equilibration studies in the presence of a reference substituted phenol. Absolute measured values (±2 SD) were: 85.2±0.5 kcal/mol for (vi-b), 84.10±0.25 kcal/mol for (vi-c), and 78.16±0.25 kcal/mol for (vi-d). As shown in Table 2, these results preliminarily indicate that substituent effects on the O—H BDE are roughly the same on going from phenols to 5-pyrimidinols.

TABLE 2

Experimental Substituent Effects on Solution-Phase O—H BDEs at 298 K of Substituted 5-Pyrimidinols (vi) and Phenols (iv)[a]

| — | 2 x ortho | para | (vi) | (iv)[c] |
|---|---|---|---|---|
| a | H | H | (91.1) | (88.3) |
| b | $CH_3$ | $CH_3$ | −5.9 | −5.6 |
| c | t-Bu | $CH_3$ | −7.0 | −7.3 |
| d | $CH_3$ | $N(CH_3)_2$ | −12.9 | d |
| a-TOH (1) | | | −10.0[e] | |

[a]All values in kcal/mol. Absolute values for Unsubstituted (vi) and (iv) are in parentheses.
[b]Estimate (see text). Could not be measured due to the short lifetime of the 5-pyrimidinoxyl radical.
[c]From ref 2C.
[d]Not an air-stable compound.

Regarding the O—H BDE of the unsubstituted 5-pyrimidinol, estimated results for (vi-b) and (vi-c) when compared to their phenolic analogues of 91.1 kcal/mol for the O—H BDE in (vi-a) are in good agreement with our calculated value of 89.6 kcal/mol. We expect this estimate to be reliable to ±1 kcal/mol.

The data indicates that (vi-d) has a lower O—H BDE than a-TOH by both theory (−0.7 kcal/mol) and experiment (−0.1 kcal/mol), but a much higher calculated IP (by 7.7 kcal/mol). This suggests that (vi-d) will transfer its phenolic H-atom to free radicals at least as fast as α-TOH, but be much more stable to air oxidation. Additionally, (vi-d) is easily prepared, handed, and purified in an open atmosphere without degradation by air oxidation—a problem commonly encountered when handling α-TOH.

Rate constants for the reactions of (vi-b–c) with alkyl radicals are determined by competition kinetics in benzene with one of either the 5-hexenyl cyclization (see Chatgilialoglu et al., *J. Am. Chem. Soc.,* 1981, 103, 7739), $k_r=1.5\times10^5$ $s^{-1}$ or neophyl radical rearrangement (see Franz et al., *J. Am. Chem. Soc.,* 1984, 106, 3964–3967; and Burton et al., *J. Org. Chem.,* 1996, 61, 3778–3782), $k_r=1.1\times10^3$ as radical clock (Table 3). Despite higher O—H BDEs for (vi-b) and (vi-c) with respect to their phenolic counterparts, their rates of reaction with alkyl radicals were substantially faster.

TABLE 3

Reactivities of Substituted Phenols and 5-Pyrimidinols to Alkyl (298 K) and Peroxyl Radicals (323 K) in Benzene[a]

| | alkyl | peroxyl |
|---|---|---|
| 6b | $4.6 \times 10^5$ (N)[c,d] | $3.3 \pm 0.4 \times 10^4$ |
| 4b | $8.5 \pm 0.2 \times 10^4$ (N)[e] | $1.1 \pm 0.1 \times 10^5$ |
| 6c | $3.2 \pm 0.5 \times 10^4$ (N) | $2.2 \pm 0.3 \times 10^4$ |
| 4c | $4.8 \pm 1.5 \times 10^3$ (N)[e] | $1.8 \pm 0.3 \times 10^4$ |

TABLE 3-continued

Reactivities of Substituted Phenols and 5-Pyrimidinols to Alkyl (298 K) and Peroxyl Radicals (323 K) in Benzene[a]

| | alkyl | peroxyl |
|---|---|---|
| 6d | $2.9 \pm 1.1 \times 10^6$ (H) | $8.6 \pm 0.5 \times 10^{6f}$ |
| a-TOH (1) | $6.0 \pm 1.5 \times 10^5$ (H)[e] | $4.1 \pm 0.4 \times 10^6$ |

[a]Radical clocks used for the reactions with alkyl radicals are indicated in parentheses.
[b]All rate constants are second order with units of $M^{-1}$ $s^{-1}$. Errors represent ± 2 SD.
[b]H = 5-hexenyl, N-neophyl.
[c]Estimate based on correlations of k and β for $CH_3CN$ (k = $5.8 \times 10^4$), EtOAc (K = $8.6 \times 10^3$) and t-BuOH (K = $4.9 \times 10^3$).[9]
[d]In 1–5% $D_2O$, $CH_3CN$, k-1.95 ± $0.7 \times 10^4$.
[d]Measurements made by L.V. and reported in ref 12.
[f]In $D_2O$-saturated benzene, k = $2.8 \pm 0.6 \times 10^6$.

Also, (vi-d), which has only a marginally lower O—H BDE than α-TOH, reacted 5 times faster with alkyl radicals. An explanation of these results may be given in terms of a polar effect in the transition state of the atom-transfer reaction. See Walling, *Free Radicals in Solution,* Wiley: New York, 1957. The pyrimidine ring better supports a partial negative charge on the aryloxyl oxygen than a phenyl ring, providing better charge separation in the transition state for H-atom transfer, and lowering the barrier to reaction for pyrimidinols compared to phenols with the same O—H BDE.

The reactivities of (vi-b) and (vi-c) with peroxyl radicals were measured by oxygen consumption experiments (see Lucarini et al., *J. Org. Chem.,* 1998, 63, 4497–4499), studying the inhibited autoxidation of styrene in benzene, and the results were compared to the values measured for 4b–c and α-TOH under the same experimental conditions. Since the rate constants for reactions with peroxyl radicals are within a factor of 3 for (vi-b)/(iv-b) and roughly the same for (vi-c)/(iv-c), a polar effect might still be involved to balance the BDE difference of 2.5–3 kcal/mol. It is, however, a smaller effect as the peroxyl oxygen cannot support a partial positive charge in the transition state as effectively as the alkyl carbon.

The reactions of (vi-b) with alkyl radicals and (vi-d) with peroxyl radicals were also performed in dry solvents containing $D_2O$ to obtain the deuterium kinetic isotope effect ($k_H/k_D$) for these reactions. In both cases, $k_H/k_D=3.1$, consistent with a primary isotope effect and suggesting that H-atom transfer is indeed the mechanism of reaction between alkyl or peroxyl radicals and the pyrimidinols.

In conclusion, by incorporating nitrogen into the aromatic ring, it is possible to substantially increase the IPs of phenolic compounds without greatly affecting their O—H BDEs. The substituent effects upon the O—H BDEs and IPs in these compounds are roughly the same as in phenol, making it possible to design novel compounds that undergo fast H-atom-transfer reactions with radicals, but which are stable to air oxidation. Moreover, the apparent presence of a kinetic polar effect in the H-atom-transfer reactions to chain-carrying radicals makes 5-pyrimidinols more effective chain-breaking antioxidants than phenols having the same O—H BDE.

The compounds of the present invention may be made combined with carriers to form compositions appropriate for the particular end use. That is, the compounds of the present invention may be administered to a subject in need of treatment by a variety of conventional routes of administration, including oral, by injection, and topical. Preferably, oral administration is by using a gel capsule.

For example, the compounds of the present invention may be made into pharmaceutical composition with an appropriate carrier easily determined by one of ordinary skill in the art and formed into a gel capsule by standard methods known in the art.

All the formulations with compounds of the present invention may be conveniently presented by any of the methods well-known in the art of pharmacy. Additionally, it will be readily apparent that the amount required of the compounds of the present invention will vary depending on the particular compound, the route of administration, and the particular treatment desired.

For topical use, the compounds of the present invention may be formulated in solutions, suspensions, gels, creams, or ointments.

As stated above, an embodiment of the present invention is to provide a method of inducing antioxidant activity in warm-blooded animals comprising administering to warm-blooded animals an antioxidatingly effective amount of a biologically active composition comprising a compound selected from the group consisting of formulae 4–11.

Another embodiment of the present invention is to provide a method of treating a pathological condition involving an oxidative stress associated with an overproduction of oxidizing free radicals, comprising administering an antioxidatively effective amount of an antioxidant comprising a compound selected from the compounds of formulae 4–11.

Another embodiment of the present invention is to provide a method of preventing free radical-mediated cellular damage in warm-blooded animals, comprising administering to warm-blooded animals an antioxidatively effective amount of a compound of formulae 4–11.

The above methods include methods of therapy involving protection of organs from oxidative damage induced by lipid peroxidation comprising administering to a subject in need of such therapy an effective amount of a compound of the formulae 4–11, or a pharmaceutically acceptable salt thereof. The organ to be protected includes the cardiovascular system or cerebral tissue. Furthermore, the subject to be treated may be recovering from myocardial infarction, or may be suffering from lung disease such as, for example, emphysema.

Additionally, the subject may have been deemed to have a predisposition for or is displaying or experiencing symptoms consistent with Parkinson's, Alzheimer's or other neurodegenerative disorder.

Another embodiment of a therapy for the above-described methods includes a therapy for treating a condition involving inhibiting the production of reactive oxygen species by activated neutrophils comprising administering to a subject in need of such therapy an effective amount of the compounds of the formulae 4–11, or a pharmaceutically acceptable salt thereof. This condition may be selected from the group consisting of psoriasis, inflammatory diseases or disorders, and AIDS.

Yet another embodiment of the above-described methods includes administering to a patient having need thereof, a compound of formulae 4–11 for the treatment of atherosclerosis and chronic inflammatory disorders; for inhibiting the peroxidation of LDL lipid; for lowering plasma cholesterol, and treating cardiovascular disease.

By way of example, the cardiovascular diseases include, but are certainly not limited to, thromboembolic disease, artherosclerosis, low density lipid oxidation, adhesion of monocytes to endothelial cells, foam-cell formation, fatty streak development, platelet adherence, platelet aggregation, smooth muscle cell proliferation, and reperfusion injury.

Also by way of example, the inflammatory diseases asthma, chronic inflammation, rheumatoid arthritis, autoimmune diabetes, transplant rejection, and tumor angiogenesis.

Another embodiment of the present invention related to a method of inhibiting oxidation of fuels, petroleum products, lubricants, rubber, polymers, chemicals, solvents, and foodstuffs. Therefore, the present invention includes a method of inhibiting the oxidation of compounds or mixtures comprising the addition of an effective amount of a compound of formulae 4–11 to said compound or mixture. The compound or mixture may be any base oil or mixture thereof suitable for the intended use of a lubricant. Also, the base oil may is selected from the group consisting of a conventionally refined mineral oil, an oil derived from coal tar or shale, a vegetable oil, an animal oil, a hydrocracked oil, or a synthetic oil, or any mixture thereof. By way of example, synthetic oils include include hydroisomerised paraffins, polyalphaolefms, polybutene, alkylbenzenes, polyglycols, esters such as polyol esters or dibasic carboxylic acid esters, alkylene oxide polymers, and silicone oils. Any petroleum product that autoxidizes is included.

In one embodiment, the compounds of the present invention may be used in the manner disclosed in U.S. Pat. No. 6,096,695 to Lam et al. with respect to being part of a effective antioxidant in lubricating oils. That is, the compounds of the present invention may be combined with the oil products in the manner suggested in the '695 patent, incorporated herein by reference.

Additionally, the compounds of the present invention may be combined with lubricating oil in the manner suggested in U.S. Pat. No. 4,946,610, incorporated herein by reference.

In that regard, the method of the present invention includes a method of reducing the oxidative environment in a petroleum composition selected from the group consisting of lubricating compositions and liquid organic fuels, said method comprising adding to said petroleum composition an effective amount of an antioxidant composition, said antioxidant composition comprising a compound formulae 4–11.

Also see U.S. Pat. No. 6,114,572 to Parker et al., incorporated by reference. The compounds of formulae 4–11 can be used, in a manner similar to the Parker compounds, as chemical antioxidant additives in organic materials normally subject to oxidative deterioration, such as, for example, rubber, plastics, fats, petroleum products and the like. In general, a preservative amount of a compound of formulae 4–11, which is sufficient in concentration to inhibit oxidative deterioration of the material to be protected, is admixed with the material subject to oxidation. The preservative amount of a compound of formula (1) will generally vary from about 0.01% to about 1.0% by weight.

Thus, another method of the present invention is inhibiting the oxidation of natural or commercial materials and products or chemical constituents thereof where compounds of the formulae 4–11 may be added, blended, sprayed, adhered, used to cover or impregnation of such products as foods (e.g. modified milk, chewing gum), feed (e.g. for livestock and other farm animals), agricultural products, drugs (e.g. oxidation inhibiting agent), non-medical drugs (e.g. preventive agent), cosmetics (e.g. hair liquid, cream, emulsion) and the raw materials thereof.

As stated in the '512 patent, the method of the present invention includes inhibiting the polymerization of compounds comprising the addition of an effective amount of compounds of the formulae 4–11 to the compound or mixture of compounds. By way of example, the product may be any of the wide variety of monomer types which undergoes free radical polymerization. Examples of said monomers include those leading to polyethylene, poly(vinyl chloride), polystyrene, styrene-butadiene rubber, butadiene-acrylonitrile copolymer, acrylonitrile-butadiene-styrene copolymer, polychloroprene, poly(methyl methacrylate), polyacrylonitrile, poly(vinyl acetate), poly(vinylidene chloride), poly(acrylic acid), poly(methacrylic acid), polyacrlyamide, polytetrafluoroethylene, polytrichlorofluoroethylene, poly(vinylidene fluoride), poly (vinyl fluoride) and allyl resins.

This invention thus being described, it will be obvious that the same may be varied in many ways. Such variations are not to be regarded as a departure from the spirit and scope of the present invention, and all such modifications as would be obvious to one of ordinary skill in the art are intended to be included within the scope of the following claims.

All cited patents and publications referred to in this application are herein expressly incorporated by reference.

What is claimed is:

1. A method of reducing the rate of oxidation in a petroleum composition or a mixture comprising:

introducing an effective amount of (i) a pyrimidine compound of the following formula and acid or base addition salts thereof, or (ii) an antioxidant composition comprising a pyrimidine compound and acid or base addition salts thereof of the following formula to said composition or mixture:

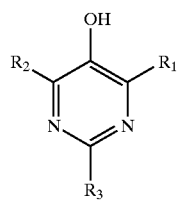

Formula 4 wherein, $R_1$ is selected from the group consisting of hydrogen, alkyl, amino, alkylamino, and N,N-dialkylamino;

$R_2$ is selected from the group consisting of hydrogen and alkyl; and $R_3$ is an electron-donating substituent.

2. The method of claim 1, wherein the petroleum composition or mixture is a base oil or mixture thereof suitable for the intended use as a lubricant.

3. The method of claim 2, wherein the base oil is selected from the group consisting of a conventionally refined mineral oil, an oil derived from coal tar or shale, a vegetable oil, an animal oil, a hydrocracked oil, a synthetic oil, or any mixture thereof.

4. The method of claim 1, wherein $R_3$ is selected from the group consisting of alkoxy, amino, N-alkylamino and N,N-dialkylamino.

5. The method of claim 1, wherein:

$R_1$ is selected from the group consisting of hydrogen and alkyl;

$R_2$ is selected from the group consisting of hydrogen, and alkyl; and $R_3$ is selected from the group consisting of alkoxy, amino, N-alkylamino, and N,N-dialkylamino.

6. The method of claim 1, wherein:

$R_1$ is selected from the group consisting of amino, N-alkylamino and N,N-dialkylamino;

$R_2$ is selected from the group consisting of hydrogen, and alkyl; and $R_3$ is selected from the group consisting of alkoxy, amino, N-alkylamino, and N,N-dialkylamino.

7. The method of claim 1, wherein the pyrimidine compound is of the following formula:

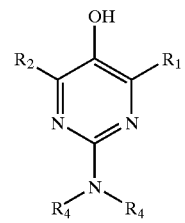

Formula 7 wherein, $R_1$ and $R_2$ are H, methyl, or t-butyl; and $R_4$ is each independently H, methyl, ethyl, t-butyl, pentyl, octyl, or phytyl.

8. The method of claim 7, wherein $R_2$ is methyl, or t-butyl.

9. The method of claim 4, wherein the pyrimidine compound is of the following formula:

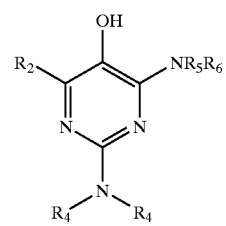

wherein, $R_2$ is H, methyl, or t-butyl;

$R_4$ is each independently H, methyl, ethyl, t-butyl, pentyl, octyl, or phytyl; and $R_5$ and $R_6$ are each independently H, methyl, t-butyl.

10. The method of claim 1, wherein the pyrimidine compound is of the following formula:

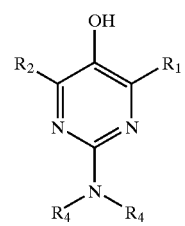

Formula 7 wherein, $R_1$, $R_2$, and $R_4$ are each independently H, or an alkyl group.

11. The method of claim 4, wherein the pyrimidine compound is of the following formula:

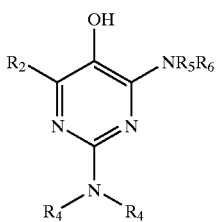

wherein, $R_2$, $R_4$, $R_5$, and $R_6$ are each independently H, or an alkyl group.

12. The method of claim 1, wherein the pyrimidine compound is 2,4,6-trimethyl-5-pyrimidinol.

13. The method of claim 1, wherein the pyrimidine compound is 2-methyl-4,6-di-tert-butyl-5-pyrimidinol.

14. The method of claim 1, wherein the pyrimidine compound is 2-methoxy-4,6-dimethyl-5-pyrimidinol.

15. The method of claim 1, wherein the pyrimidine compound is 2-N,N-dimethylamino-4,6-dimethyl-5-pyrimidinol.

16. The method of claim 1, wherein the composition in which oxidation is inhibited is a petroleum composition selected from the group consisting of lubricating compositions and liquid organic fuels, and:

the introducing step reduces the oxidative environment in the petroleum composition.

17. The method of claim 1, wherein the petroleum composition or mixture is a liquid organic fuel.

18. The method of claim 1, wherein the petroleum composition or mixture is a lubricant, rubber, polymer, solvent.

19. A method of stabilizing monomers, comprising: introducing an polymerization inhibiting effective amount of effective amount of (i) a pyrimidine compound of the following formula and acid or base addition salts thereof, or (ii) an antioxidant composition comprising a pyrimidine compound and acid or base addition salts thereof of the following formula to a monomer:

Formula 4

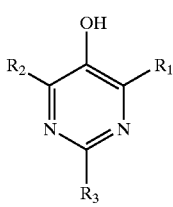

wherein, $R_1$ is selected from the group consisting of hydrogen, alkyl, amino, alkylamino, and N,N-dialkylamino;

$R_2$ is selected from the group consisting of hydrogen and alkyl; and $R_3$ is an electron-donating substituent.

20. The method of claim 19, wherein said monomer leads to polyethylene, poly(vinyl chloride), polystyrene, styrene-butadiene rubber, butadiene-acrylonitrile copolymer, acrylonitrile-butadiene-styrene copolymer, polychloroprene, poly(methyl methacrylate), polyacrylonitrile, poly(vinyl acetate), poly(vinylidene chloride), poly(acrylic acid), poly methacrylic acid), polyacrylamide, polytetrafluoroethylene, polytrichlorofluoroethylene, poly(vinylidene fluoride), polyvinyl fluoride), allyl resins.

21. The method of claim 19, wherein $R_3$ is selected from the group consisting of alkoxy, amino, N-alkylamino and N,N-dialkylamino.

22. The method of claim 19, wherein, $R_1$ is selected from the group consisting of hydrogen and alkyl;

$R_2$ is selected from the group consisting of hydrogen, and alkyl; and $R_3$ is selected from the group consisting of alkoxy, amino, N-alkylamino, and N,N-dialkylamino.

23. The method of claim 19, wherein, $R_1$ is selected from the group consisting of amino, N-alkylamino and N,N-dialkylamino;

$R_2$ is selected from the group consisting of hydrogen, and alkyl; and $R_3$ is selected from the group consisting of alkoxy, amino, N-alkylamino, and N,N-dialkylamino.

24. The method of claim 19, wherein the pyrimidine compound is of the following formula:

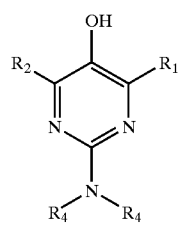

wherein, $R_1$ and $R_2$ are H, methyl, or t-butyl; and $R_4$ is each independently H, methyl, ethyl, t-butyl, pentyl, octyl, or phytyl.

25. The method of claim 19, wherein $R_2$ is methyl, or t-butyl.

26. The method of claim 19, wherein the pyrimidine compound is of the following formula:

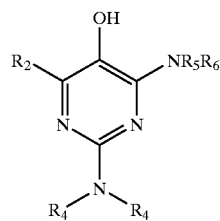

wherein, $R_2$ is H, methyl, or t-butyl;

$R_4$ is each independently H, methyl, ethyl, t-butyl, pentyl, octyl, or phytyl; and $R_5$ and $R_6$ are each independently H, methyl, t-butyl.

27. The method of claim 19, wherein the pyrimidine compound is of the following formula:

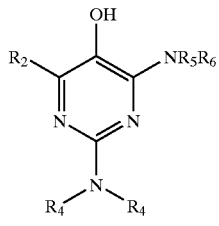

wherein, $R_2$, $R_4$, $R_5$, and $R_6$ are each independently H, or an alkyl group.

28. A method of inhibiting the oxidation of a polymer, comprising:

introducing an effective amount of (i) a pyrimidine compound of the following formula and acid or base addition salts thereof, or (ii) an antioxidant composition comprising a pyrimidine compound and acid or base addition salts thereof of the following formula to the polymer:

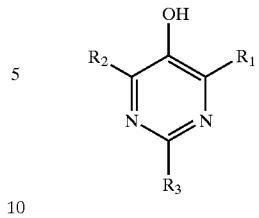

Formula 4 wherein, $R_1$ is selected from the group consisting of hydrogen, alkyl, amino, alkylamino, and N,N-dialkylamino;

$R_2$ is selected from the group consisting of hydrogen and alkyl; and $R_3$ is an electron-donating substituent.

29. The method of claim 28, wherein $R_3$ is selected from the group consisting of alkoxy, amino, N-alkylamino and N,N-dialkylamino.

* * * * *